United States Patent
Kawahara

(10) Patent No.: US 8,330,949 B2
(45) Date of Patent: Dec. 11, 2012

(54) FOREIGN SUBSTANCE INSPECTION APPARATUS, EXPOSURE APPARATUS, AND METHOD OF MANUFACTURING DEVICE

(75) Inventor: Atsushi Kawahara, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 338 days.

(21) Appl. No.: 12/871,368

(22) Filed: Aug. 30, 2010

(65) Prior Publication Data

US 2011/0051130 A1    Mar. 3, 2011

(30) Foreign Application Priority Data

Aug. 31, 2009   (JP) ................. 2009-201084

(51) Int. Cl.
*G01N 21/00* (2006.01)
*G01N 15/02* (2006.01)

(52) U.S. Cl. ............ 356/237.3; 356/237.1; 356/336

(58) Field of Classification Search .......... 356/335–344, 356/237.1–241.6, 242.1–243.8, 426–431, 356/600–640
See application file for complete search history.

(56) References Cited

U.S. PATENT DOCUMENTS

| | | | |
|---|---|---|---|
| 4,740,079 A * | 4/1988 | Koizumi et al. | ........... 356/237.4 |
| 5,581,348 A | 12/1996 | Miura et al. | |
| 5,585,916 A | 12/1996 | Miura et al. | |
| 6,493,097 B1 * | 12/2002 | Ivarsson | ........... 356/630 |
| 7,256,412 B2 * | 8/2007 | Nishiyama et al. | ........ 250/559.4 |
| 2003/0035149 A1 * | 2/2003 | Ishikawa et al. | ........... 358/302 |

FOREIGN PATENT DOCUMENTS

| | | |
|---|---|---|
| JP | 7-005115 A | 1/1995 |
| JP | 7-043312 A | 2/1995 |

* cited by examiner

*Primary Examiner* — Gregory J Toatley
*Assistant Examiner* — Jarreas C Underwood
(74) *Attorney, Agent, or Firm* — Rossi, Kimms & McDowell LLP

(57) ABSTRACT

A foreign substance inspection apparatus includes a light projecting unit, a detector which detects the intensity of scattered light of light projected onto the surface of an object to be detected by the light projecting unit, in association with the two-dimensional coordinate position on the surface, and a processing unit. The relationship between the intensity of the scattered light detected by the detector and the particle size of the foreign substance differs depending on the two-dimensional coordinate position on the surface. The processing unit determines, a conversion curve to convert the intensity of the scattered light detected by the detector into the particle size of the foreign substance, in accordance with the two-dimensional coordinate position of the foreign substance detected by the detector, and converts the intensity of the scattered light detected by the detector into the particle size of the foreign substance using the determined conversion curve.

7 Claims, 9 Drawing Sheets

FIG. 1
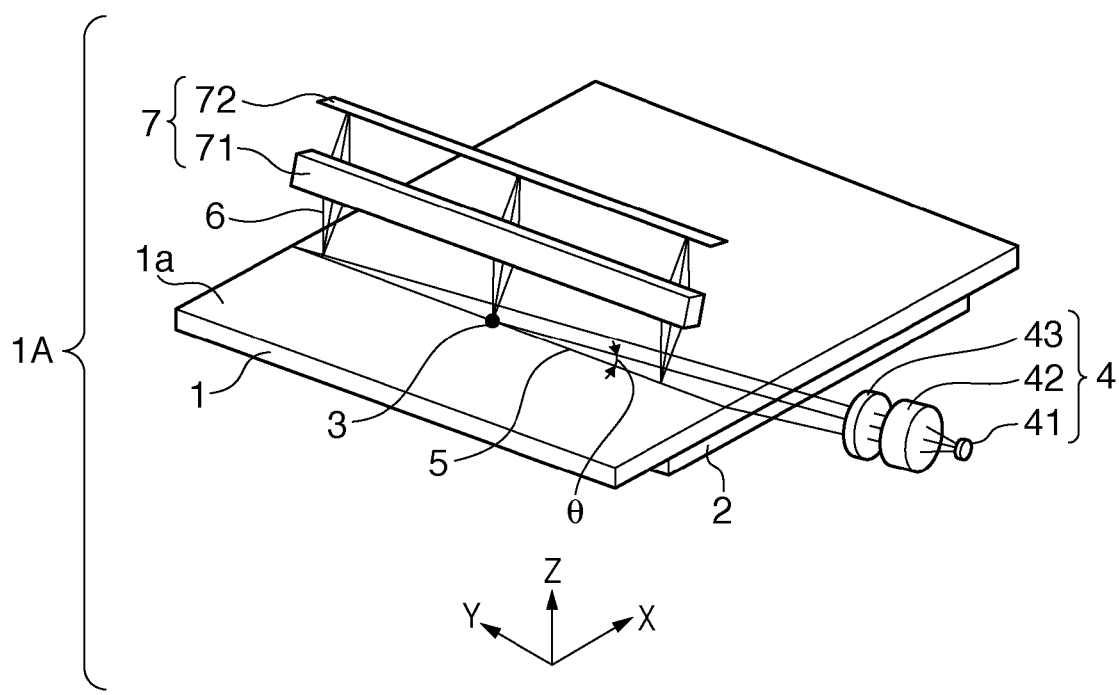
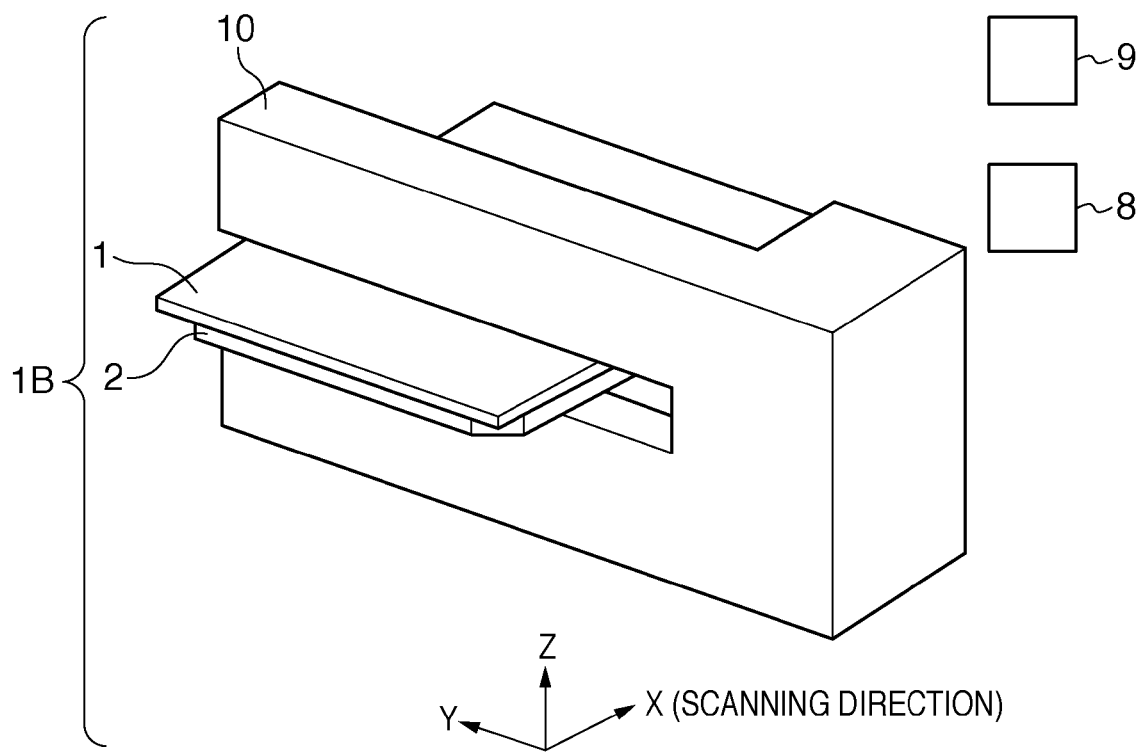
X (SCANNING DIRECTION)

FIG. 2

FOREIGN SUBSTANCE

EXAMPLE OF INSPECTION MAP

KNOWN FOREIGN SUBSTANCE INFORMATION

8A →

| COORDINATE POSITION | PARTICLE SIZE (μm) |
|---|---|
| (1, 1) | 10.0 |
| (1, 1) | 20.0 |
| (1, 1) | 30.0 |
| (1, 1) | 40.0 |
| (1, 2) | 10.0 |
| (1, 2) | 20.0 |
| (1, 2) | 30.0 |
| (1, 2) | 40.0 |
| (1, 3) | 10.0 |
| (1, 3) | 20.0 |
| (1, 3) | 30.0 |
| (1, 3) | 40.0 |
| (1, 4) | 10.0 |
| (1, 4) | 20.0 |
| (1, 4) | 30.0 |
| (1, 4) | 40.0 |
| ⋮ | ⋮ |
|  |  |

DETECTED FOREIGN SUBSTANCE

← 8B

| COORDINATE POSITION | DETECTION VOLTAGE (V) |
|---|---|
| (1, 1) | 0.2 |
| (1, 1) | 0.4 |
| (1, 1) | 0.7 |
| (1, 1) | 1.2 |
| (1, 2) | 0.1 |
| (1, 2) | 0.3 |
| (1, 2) | 0.8 |
| (1, 2) | 1.5 |
| (1, 3) | 0.5 |
| (1, 3) | 0.8 |
| (1, 3) | 1.2 |
| (1, 3) | 1.8 |
| (1, 4) | 0.4 |
| (1, 4) | 0.7 |
| (1, 4) | 1.0 |
| (1, 4) | 1.6 |
| ⋮ | ⋮ |
|  |  |

CONVERSION CURVES AT COORDINATE POSITIONS (1, 1) TO (1, 4)

8C →

FOREIGN SUBSTANCE INSPECTION APPARATUS, EXPOSURE APPARATUS, AND METHOD OF MANUFACTURING DEVICE

BACKGROUND OF THE INVENTION

1. Field of the Invention

The present invention relates to a foreign substance inspection apparatus, which efficiently detects foreign substances on a reticle called a photomask or on a protective film called a pellicle, an exposure apparatus having the inspection apparatus, and a method of manufacturing a device. The reticle has a circuit pattern formed on it, which is used to manufacture a device, for example, a semiconductor device such as an integrated circuit or a large-scale integration, a charge-coupled device, a liquid crystal panel, or a magnetic head. The pellicle is a protective cover attached to the reticle in order to prevent any foreign substances from adhering onto the reticle.

2. Description of the Related Art

In the process of manufacturing a device, an exposure apparatus (a stepper or a mask aligner) generally transfers a circuit pattern formed on a reticle onto a wafer coated with a resist. During this transfer, if a pattern defect or a foreign substance such as dirt is present on the reticle, the pattern defect or the foreign substance is transferred onto the wafer, together with the circuit pattern, which lowers the device manufacturing yield. Especially when a large number of circuit patterns are repeatedly printed on a wafer by the step & repeat method using a reticle, one harmful foreign substance, if any, on the reticle is printed on the entire wafer, and this considerably lowers the device yield. Hence, in the process of manufacturing a device, it is necessary to detect the presence of foreign substances on the reticle. An inspection method which uses a property that a foreign substance isotropically scatters light is commonly adopted for this detection. For example, some schemes inspect a surface to be inspected by obliquely applying a parallel light beam onto the surface to be inspected from above, and guiding the light scattered by a foreign substance onto a one-dimensional image sensor (to be referred to as a "line sensor" hereinafter) in a gradient index microlens array to image the foreign substance on the sensor. Japanese Patent Laid-Open Nos. 7-43312 and 7-5115 disclose details of these schemes.

To convert the detected intensity of scattered light into the particle size of a foreign substance, the conventional foreign substance inspection apparatus uses a histogram of a detection signal obtained upon inspecting a test reticle coated with reference particles. A plurality of test reticles are used for respective types of reference particles with different sizes (e.g., 10 µm, 20 µm, 30 µm, and 40 µm). The inspection apparatus inspects the test reticles for foreign substances, and calculates the frequency distributions (to be referred to as "histograms" hereinafter) of the detection voltages. The inspection apparatus then reads most representative detection voltages from the histograms for respective types of reference particles, and determines a conversion table to convert the detection voltage into the particle size of a foreign substance. The inspection apparatus also interpolates using discrete data of the conversion table to obtain a conversion curve.

However, the conventional inspection apparatus uses a table or curve common to the entire region on an inspection surface based on histograms, so it can obtain only one average conversion table or conversion curve for each inspection surface. Thus, unless the intensity of scattered light and the particle size of a foreign substance, detected by the inspection apparatus, have a uniform relationship within the plane of the inspection surface, the exact particle size of the foreign substance cannot be obtained.

SUMMARY OF THE INVENTION

The present invention provides a foreign substance inspection apparatus, which is capable of precisely obtaining the particle sizes of foreign substances over the entire region on an inspection surface.

According to the present invention, there is provided a foreign substance inspection apparatus which includes a light projecting unit that projects light onto a surface of an object to be detected, a detector that detects an intensity of scattered light as a component of the light, projected onto the surface by the light projecting unit, in association with a two-dimensional coordinate position on the surface, and a processing unit that determines a particle size of a foreign substance present on the surface based on the detection result obtained by the detector, wherein a relationship between the intensity of the scattered light detected by the detector and the particle size of the foreign substance differs depending on the two-dimensional coordinate position on the surface, and the processing unit determines, a conversion curve to convert the intensity of the scattered light detected by the detector into the particle size of the foreign substance, in accordance with the two-dimensional coordinate position of the foreign substance detected by the detector, and converts the intensity of the scattered light detected by the detector into the particle size of the foreign substance using the determined conversion curve.

Further features of the present invention will become apparent from the following description of exemplary embodiments with reference to the attached drawings.

BRIEF DESCRIPTION OF THE DRAWINGS 1A and 1B in FIG. 1 are schematic perspective views of an inspection apparatus;

FIG. 2 is a view illustrating an example of an inspection map;

Figure 4:
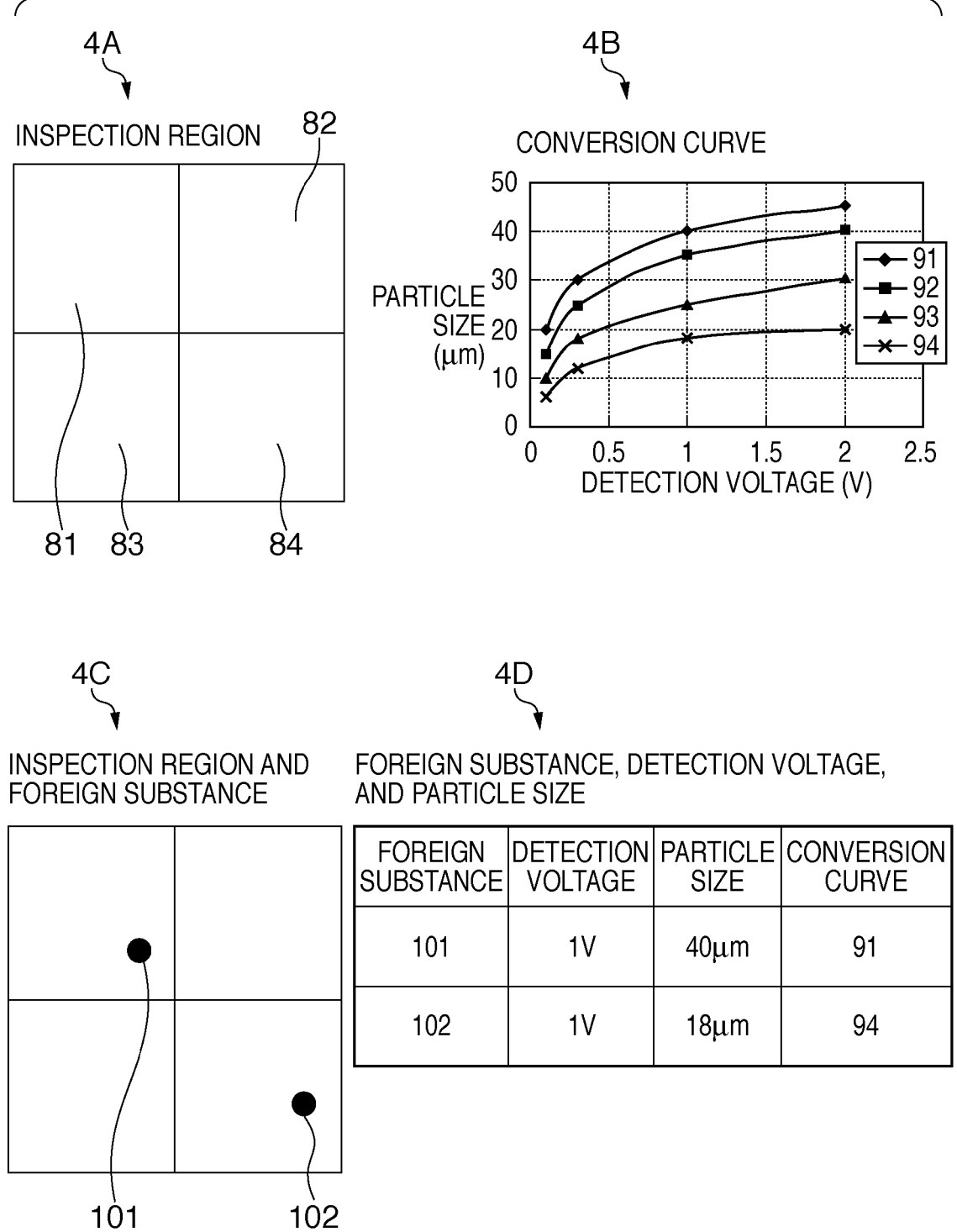
Figure 5:
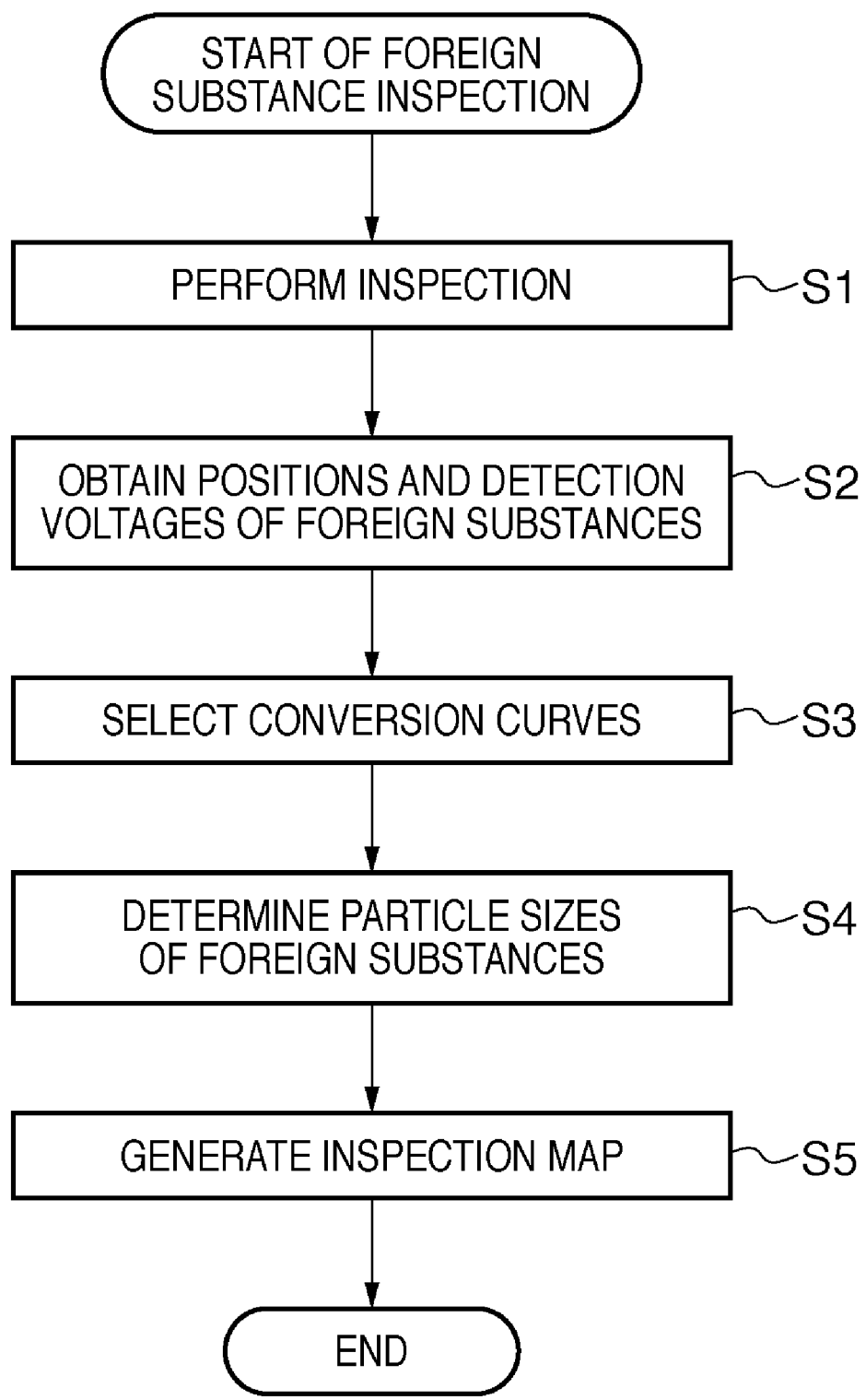
Figure 6:
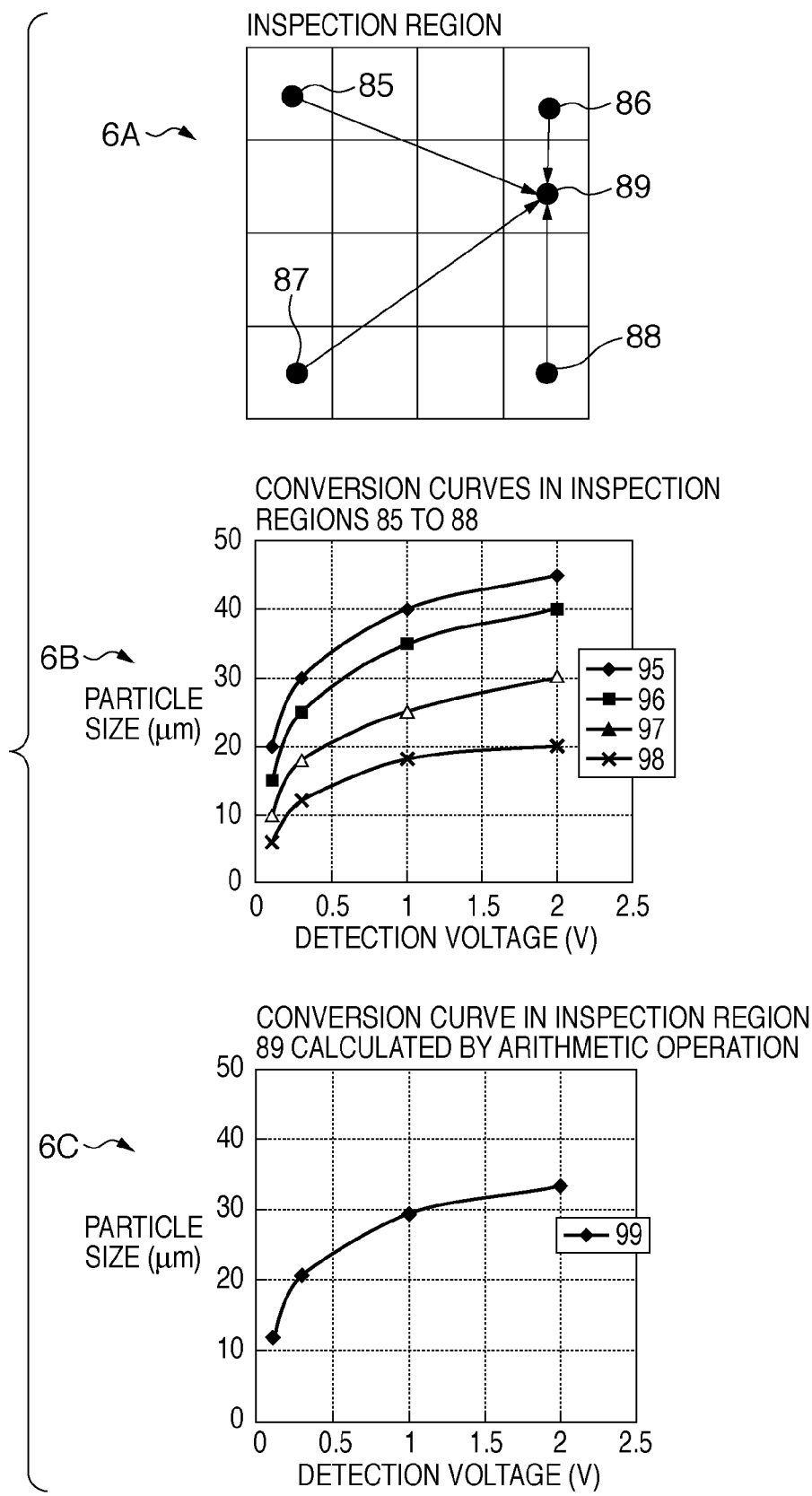
Figure 7:
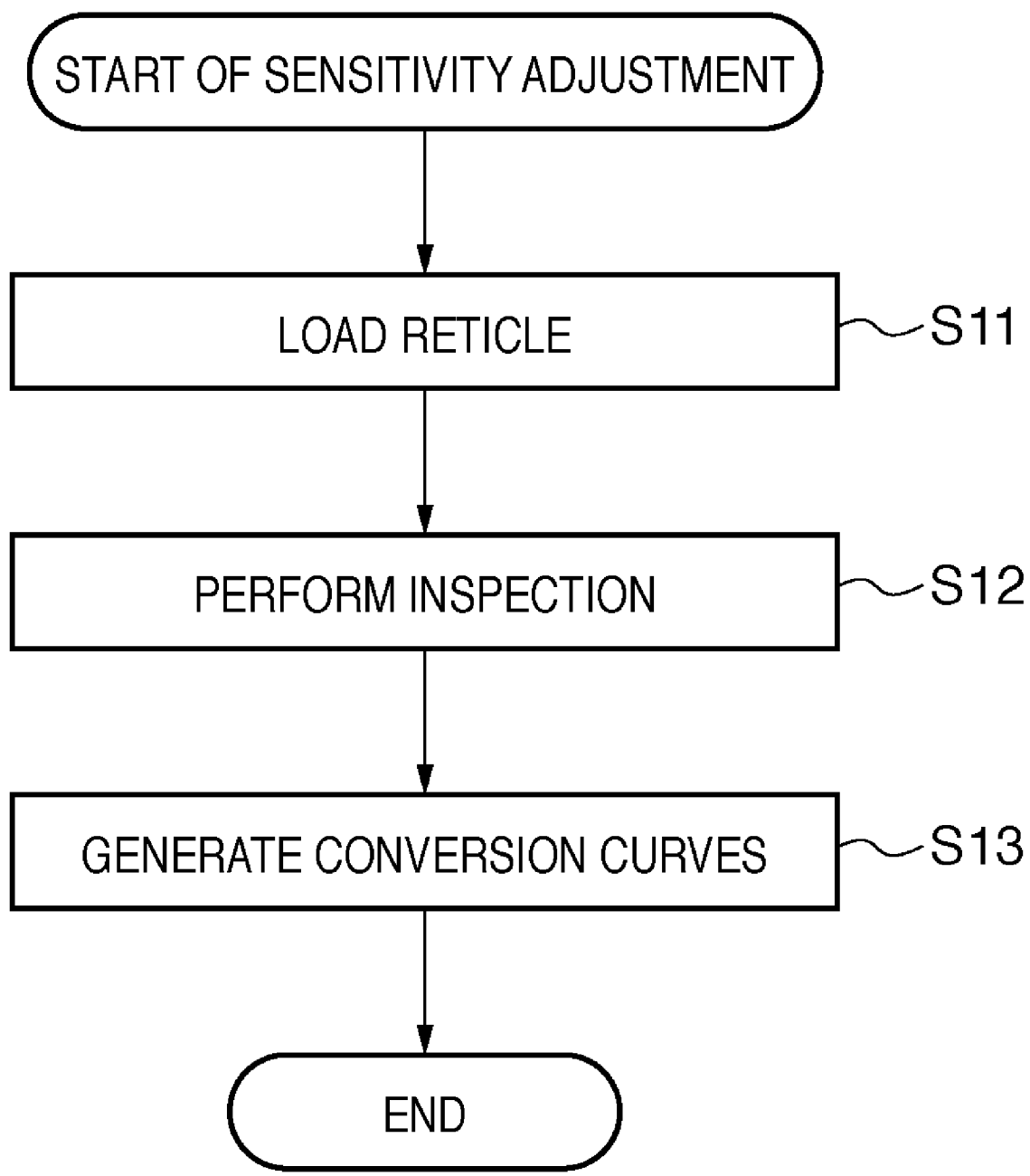
Figure 8:
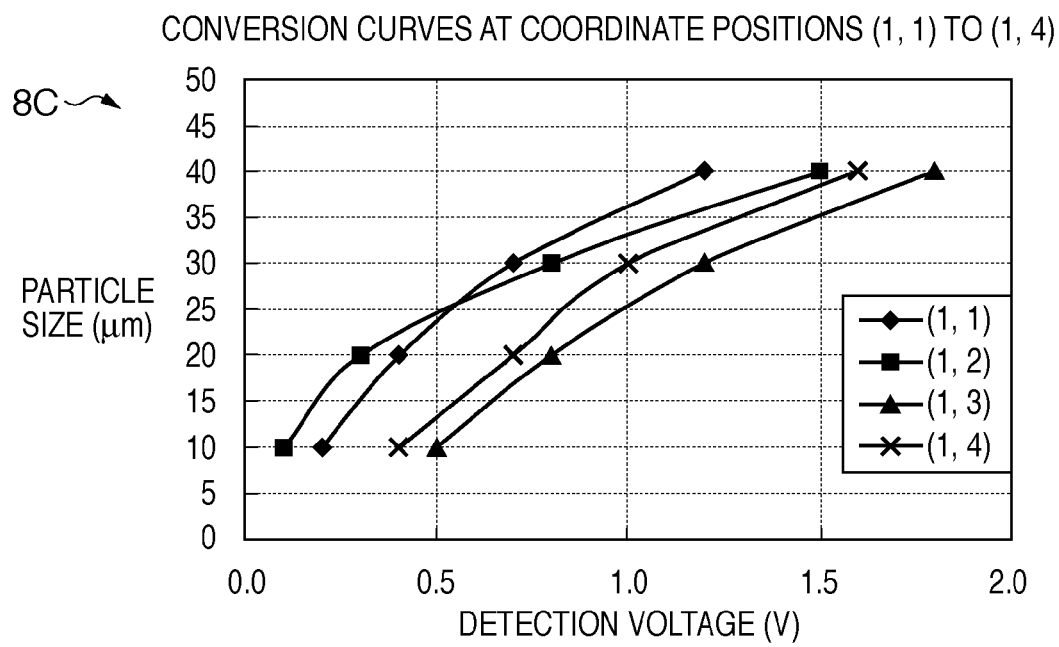

4A to 4D in FIG. 4 are views for explaining the first embodiment;

FIG. 5 is a flowchart showing the process sequence of an inspection apparatus according to the first embodiment;

6A to 6C in FIG. 6 are views for explaining the second embodiment;

FIG. 7 is a flowchart showing the process sequence of an inspection apparatus according to the third embodiment;

8A to 8C in FIG. 8 are views for explaining the third embodiment; and

Figure 9:
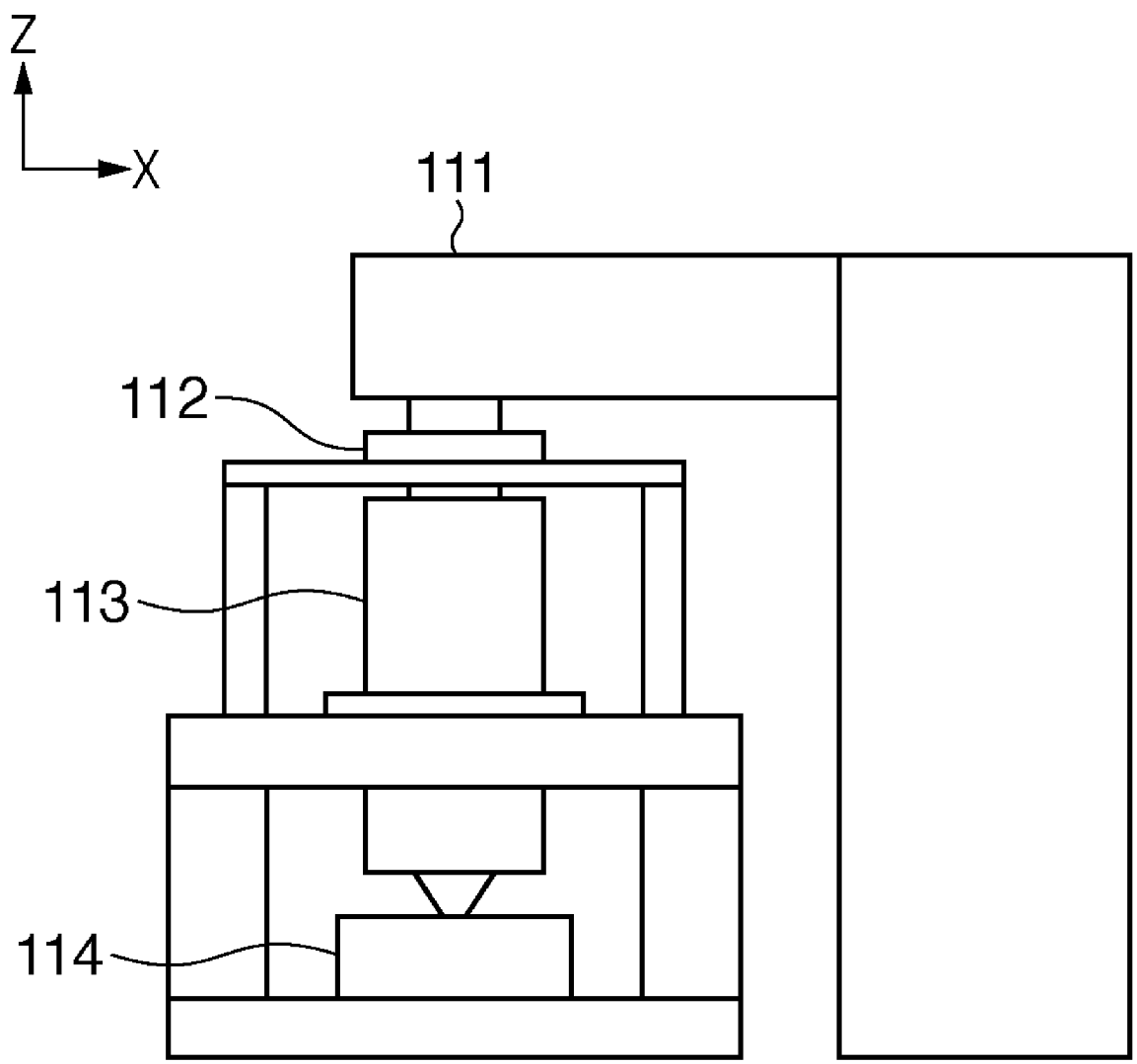

FIG. 9 is a schematic view of an exposure apparatus.

DESCRIPTION OF THE EMBODIMENTS

Embodiments of the present invention will be described in detail below with reference to the accompanying drawings. Note that the following embodiments are merely examples, and can be modified or changed as needed in accordance with the arrangement of an apparatus to which the present invention is applied, and various kinds of conditions involved.

1A and 1B in FIG. 1 show the state in which a foreign substance inspection apparatus inspects the surface of a reticle 1 as an object to be detected for a foreign substance. 1B in FIG. 1 shows the entire inspection apparatus, and 1A in FIG. 1 shows the basic configuration of an optical system for detecting a foreign substance by inspection in the inspection apparatus. For the sake of descriptive simplicity, 1A in FIG. 1 shows only an optical system for inspecting a blank surface 1a of the reticle 1 for a foreign substance. In practice, however, the inspection apparatus also includes an optical system for inspecting for a foreign substance a pellicle film which protects the circuit pattern surface of the reticle 1 against any foreign substances. In 1A and 1B in FIG. 1, reference numeral 2 denotes a pellicle frame which mounts the pellicle frame. A light beam, with a given angle of divergence, emitted by a semiconductor laser 41 is collimated into a parallel light beam by a collimator lens 42. The parallel light beam is incident on a surface to be inspected at an incident angle Θ close to 90° with respect to the surface to be inspected via a λ/2 plate 43. In this way, a rectilinear illumination region 5 is formed by the laser beam on the blank surface 1a as the surface to be inspected. If a foreign substance 3 is present on the blank surface 1a in the illumination region 5, it scatters light 6. The scattered light 6 is focused on a line sensor 72 by an imaging lens 71 (lens array) in which lenses are arrayed in the longitudinal direction of the illumination region 5. The imaging lens 71 is configured to image the illumination region 5 on the line sensor 72. The line sensor 72 includes a plurality of photoelectric conversion elements positioned on it in a first direction (Y direction). The line sensor 72 and imaging lens 71 constitute a detector 7 which detects the intensity of scattered light as a component of light, projected onto the surface of the object to be detected, in association with the two-dimensional coordinate position on the surface. Also, the semiconductor laser 41, collimator lens 42, and λ/2 plate 43 constitute a light projecting unit 4 which projects light onto the surface of the object to be detected.

Figure 2:
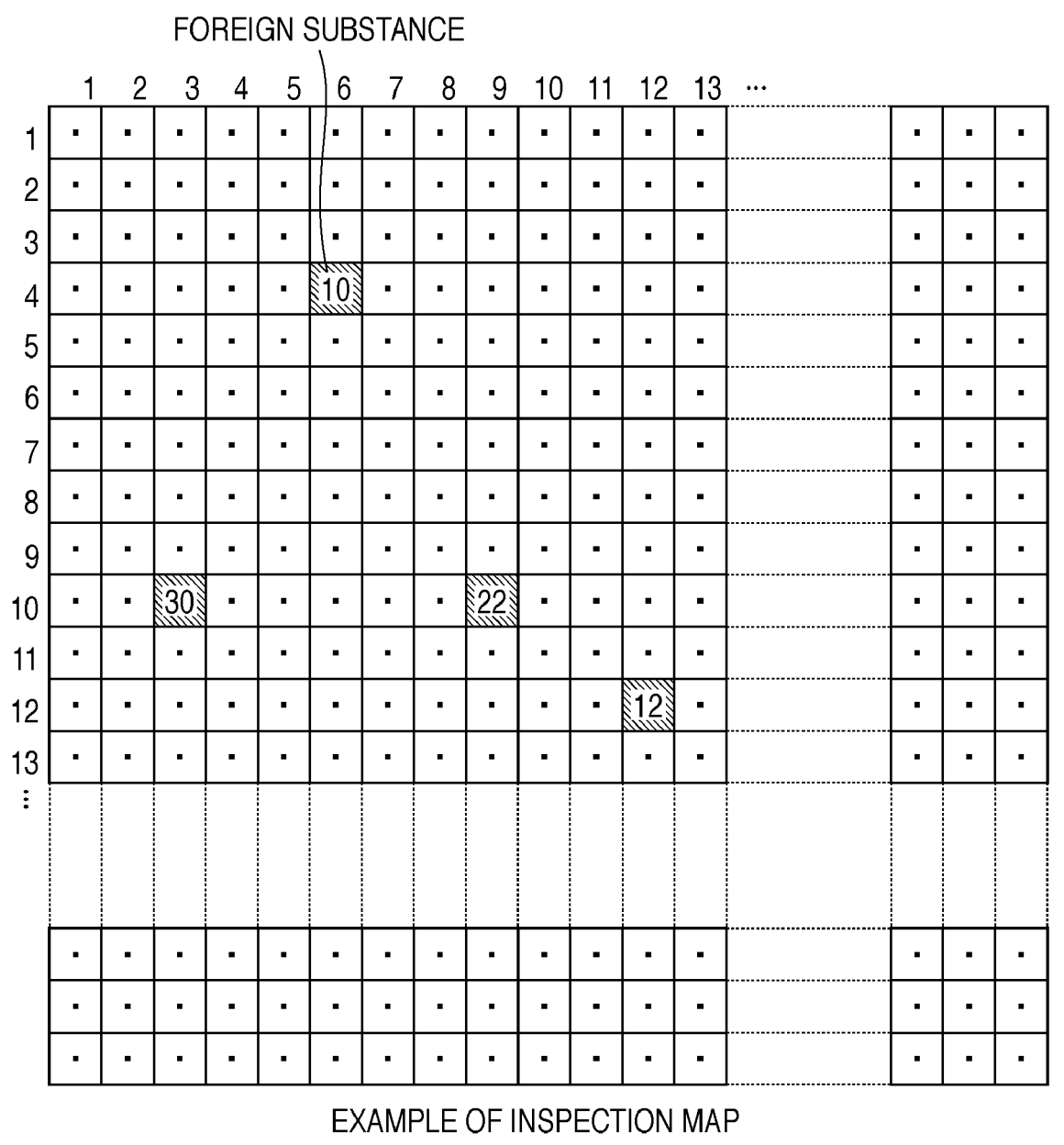

As shown in 1B in FIG. 1, the blank surface 1a is inspected as a whole for foreign substances by scanning an entire optical system 10 in a second direction perpendicular to the first direction (Y direction), that is, in the X direction by a driving unit 9 which drives the entire optical system 10 relative to the blank surface 1a in the X direction. The detection result obtained by the line sensor 72 is input to a processing unit 8. The processing unit 8 tabulates the signals input from the line sensor 72 during the scanning of the entire optical system 10 to generate an inspection map corresponding to the line sensor 72. The processing unit 8 determines the exact positions and sizes of the foreign substances after the foreign substance inspection. FIG. 2 illustrates an example of the inspection map generated by the processing unit 8. The inspection map is obtained by dividing the inspection region into small segments, and indicating the representative value of the particle size of the foreign substance detected for each segment. The small segments are typically 1×1-mm to 5×5-mm grids. Common inspection apparatuses perform specific ranking after converting the detection signal values into the particle sizes, and examine the inspection record using the tabulation result of the number of foreign substances for each rank.

Figure 3:
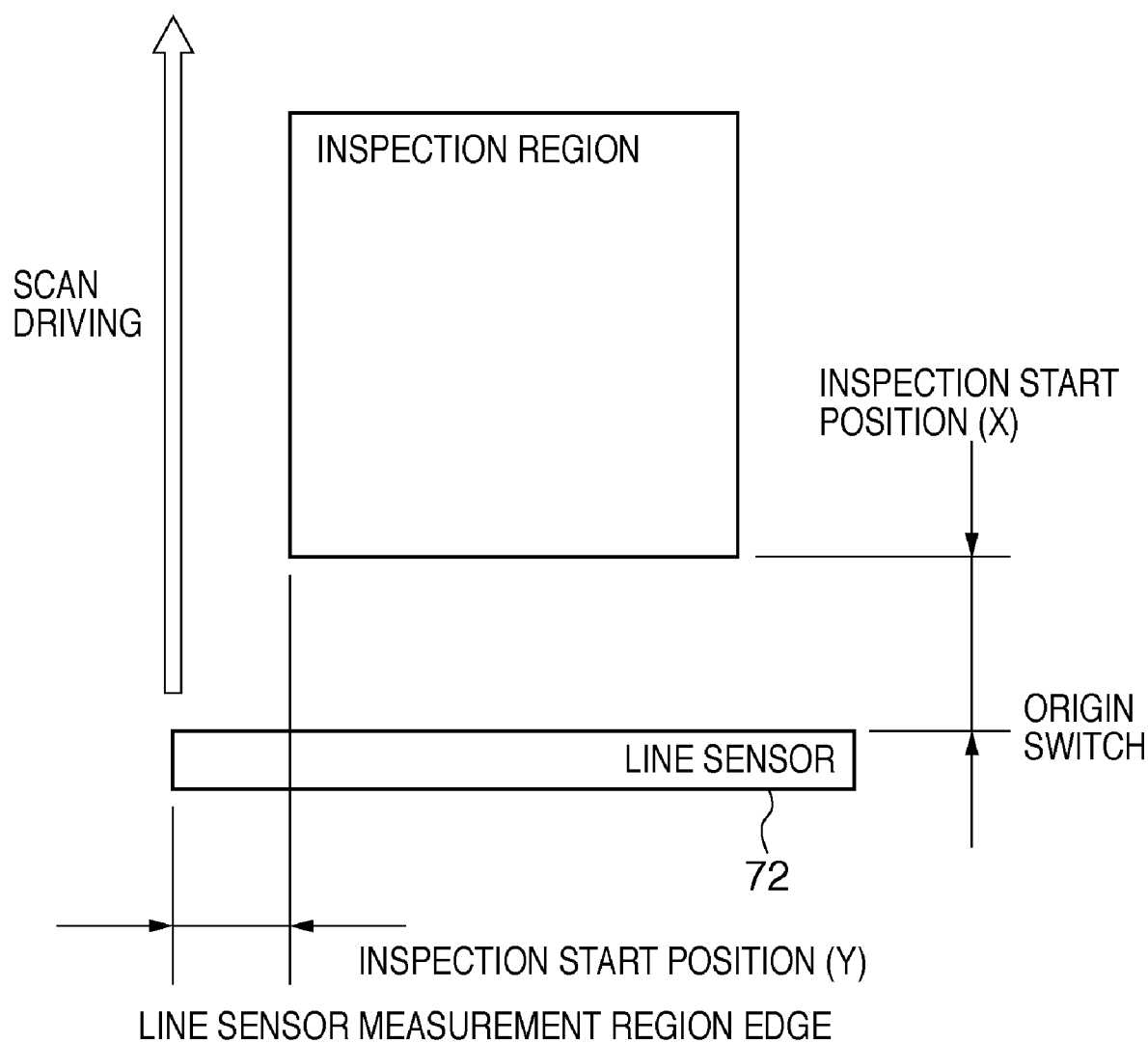
FIG. 3 is a conceptual view of the inspection start position in the inspection region.

A basic method to control the inspection start position in the inspection apparatus will be described with reference to FIG. 3. The inspection start position in the scanning direction is controlled using its distance from an origin switch placed at the scanning start position. The longitudinal direction of the line sensor 72 is controlled using its distance from a point on the measurement edge of the line sensor 72. The origin switch and the line sensor 72 have attachment errors, so only foreign substances which fall within a predetermined range on a reticle placed in the inspection apparatus are detected by inspection by adjusting the inspection start position for each line sensor during assembly of the inspection apparatus.

First Embodiment

A method of determining the particle size of a foreign substance by an inspection apparatus will be described with reference to 4A to 4D in FIGS. 4 and 5. 4A and 4B in FIG. 4 illustrate an example of the regions where foreign substances are detected by inspection, and conversion curves. The relationship between the intensity of scattered light detected by a line sensor 72 and the particle size of a foreign substance differs depending on the two-dimensional coordinate position on an inspection surface. In the first embodiment, the inspection surface is divided into four regions: regions 81 to 84, and a processing unit 8 of the inspection apparatus holds a plurality of conversion curves 91 to 94 corresponding to the plurality of regions 81 to 84, respectively. 4C and 4D in FIG. 4 are views for explaining a method of calculating the particle size of a foreign substance by selecting a conversion curve in the region to which the two-dimensional coordinate position of the detected foreign substance belongs. 4C in FIG. 4 shows foreign substances 101 and 102 adhering on the inspection surface. 4D in FIG. 4 shows the associations among the detection voltages of the foreign substances 101 and 102, the conversion curves 91 and 94 selected by taking account of the adhesion positions of the foreign substances 101 and 102, respectively, and the particle sizes of the foreign substances 101 and 102 calculated using the conversion curves 91 and 94, respectively.

FIG. 5 illustrates an example of the process sequence when the inspection surface shown in 4C in FIG. 4 is inspected for foreign substances. In step S1, the inspection apparatus inspects the inspection surface for foreign substances. In step S2, a detector 7 obtains the two-dimensional coordinate positions of the adhesion positions of the foreign substances 101 and 102, and detection voltages corresponding to the light beams scattered by the foreign substances 101 and 102. The detection voltages of the foreign substances 101 and 102 are both 1 V. In step S3, the processing unit 8 selects conversion curves used to calculate the particle sizes of the detected foreign substances in accordance with their two-dimensional coordinate positions. The processing unit 8 selects the conversion curve 91 corresponding to the region 81 for the foreign substance 101, and selects the conversion curve 94 corresponding to the region 84 for the foreign substance 102. In step S4, the processing unit 8 calculates the particle sizes of the foreign substances 101 and 102 using the conversion curves 91 and 94, respectively. From the fact that the foreign substance 101 has a detection voltage of 1 V and the conversion curve 91, its particle size is found to be 40 μm. From the fact that the foreign substance 102 has a detection voltage of 1 V and the conversion curve 94, its particle size is found to be 18 μm. In step S5, the processing unit 8 generates an inspection map from the detection positions obtained in step S2, and the particle size information calculated in step S4. Using the above-mentioned process sequence, the inspection apparatus can detect the particle sizes of foreign substances by inspection with high precision.

In the above-mentioned embodiment, the inspection surface is divided into four regions. If the processing unit 8 holds only two conversion curves corresponding to the two-dimensional coordinate positions on the inspection surface, the inspection surface may be divided into only two regions. Conversely, if the processing unit 8 holds five or more conversion curves, the inspection surface may be divided into five or more regions. Also, although a conversion curve given by the function of the detection voltage vs. the particle size of a foreign substance is adopted in the above-mentioned embodiment, a conversion table indicating the association between the detection voltage and the particle size of a foreign substance may be adopted instead.

Second Embodiment

The second embodiment will be described with reference to FIGS. 5 and 6A to 6C in FIG. 6. In the second embodiment, the inspection surface is divided into, for example, 16 regions, as shown in 6A in FIG. 6. A processing unit 8 of an inspection apparatus stores conversion curves 95, 96, 97, and 98 corresponding to four regions 85, 86, 87, and 88, respectively, as shown in 6B in FIG. 6. However, the processing unit 8 holds no conversion curves in regions other than the four regions 85 to 88. In step S1, the inspection apparatus inspects the inspection surface for foreign substances. In step S2, a detector 7 obtains the positions of the foreign substances adhering on the inspection surface, and their detection voltages. In step S3, the processing unit 8 of the inspection apparatus selects or calculates conversion curves used to determine the particle sizes of the foreign substances. The processing unit 8 selects the conversion curves 95 to 98 corresponding to the regions 85 to 88, respectively, for the foreign substances within the regions 85 to 88. If a foreign substance has a two-dimensional coordinate position which falls within a region other than the regions 85 to 88, the processing unit 8 determines a conversion curve at an arbitrary point other than the regions 85 to 88 from the distances between that point and points representative of the regions 85 to 88, and the information of the conversion curves 95 to 98.

Let n (n=4 in this embodiment) be the number of regions 85 to 88 having conversion curves, $(x_i, y_i)$ be the coordinate positions of points which fall within the plurality of regions and are representative of these regions, and $S_i$ be the conversion curves in the plurality of regions, which have already been held in the processing unit 8. Note that i=1 to n. Also, let (x,y) be the coordinate position of an arbitrary point which falls outside the plurality of regions 85 to 88, and S be the conversion curve at the arbitrary point. Then, the processing unit 8 determines the conversion curve S at the arbitrary point by weighting the known conversion curve $S_i$ by the reciprocal of its distance from a point representative of a region corresponding to the known conversion curve $S_i$ using:

$$S = \frac{\sum_{i=1}^{n} [S_i \times \{(x-x_i)^2 + (y-y_i)^2\}^{-0.5}]}{\sum_{i=1}^{n} \{(x-x_i)^2 + (y-y_i)^2\}^{-0.5}}$$

In step S4, the processing unit 8 determines the particle sizes of the foreign substances using the conversion curves selected or determined from the conversion curves held in it in advance. In step S5, the processing unit 8 generates an inspection map from the detection positions obtained in step S2, and the particle sizes determined in step S4. Although the calculation of conversion curves corresponding to the divided inspection regions is done in step S3 in the above-mentioned embodiment, it may be done before step S1.

Third Embodiment

An embodiment in which conversion curves are generated will be described with reference to FIGS. 7 and 8A to 8C in FIG. 8. FIG. 7 illustrates an example of the sequence of a process of generating conversion curves by an inspection apparatus. 8A to 8C in FIG. 8 illustrate an example of foreign substance information and conversion curves referred to in an explanation of the process sequence. The inspection apparatus sets a coordinate position for each 1×1-mm grid defined on the inspection surface, as shown in the inspection map of FIG. 2. Although a coordinate position is set for each 1×1-mm grid in the third embodiment, the grid size can be changed in accordance with the number of division of the area of the inspection region. The inspection apparatus holds a storage area for grid-specific conversion curves. In step S11, a test reticle is loaded into the inspection apparatus. The test reticle is coated with foreign substances with specific particle sizes at specific coordinate positions defined on it, shown in 8A in FIG. 8. In step S12, the test reticle is inspected for foreign substances using the inspection apparatus. 8B in FIG. 8 shows the detection voltage of the foreign substance at each coordinate position. In step S13, a processing unit 8 of the inspection apparatus calculates a conversion curve at each coordinate position from the foreign substance information shown in 8A in FIG. 8, and the detection voltage shown in 8B in FIG. 8. 8C in FIG. 8 illustrates an example of conversion curves at the calculated coordinate positions (1,1) to (1,4). The use of the thus calculated conversion curves makes it possible to detect the particle sizes of foreign substances by inspection with high precision.

The present invention is applicable not only to a foreign substance inspection apparatus used to manufacture, for example, a semiconductor device or a liquid crystal display device, but also to sensitivity adjustment of, for example, various kinds of high-precision processing apparatuses and various kinds of high-precision measurement apparatuses. Hence, the present invention is effective in detecting foreign substances on a processing object or on the surface to be inspected of an object to be measured.

Description of Exposure Apparatus

An exemplary exposure apparatus which transfers the pattern of a reticle onto a substrate to expose the substrate, and to which a foreign substance inspection apparatus in one of the above-mentioned embodiments is applied will be described. The exposure apparatus includes an illumination system 111, a reticle stage 112 which mounts a reticle, a projection optical system 113, and a substrate stage 114 which holds a substrate, as shown in FIG. 9. The substrate stage 114 is moved by scanning in the Y direction and moved in steps in the X direction by a driving mechanism (not shown), as described earlier. The exposure apparatus projects a circuit pattern formed on a reticle onto a substrate to scan-expose the substrate. The illumination system 111 illuminates a reticle on which a circuit pattern is formed, and includes a light source unit and illumination optical system. The light source unit uses, for example, a laser as a light source. The laser used can be, for example, an ArF excimer laser with a wavelength of about 193 nm, a KrF excimer laser with a wavelength of about 248 nm, or an $F_2$ laser with a wavelength of about 153 nm. However, the type of laser is not limited to an excimer laser, and a YAG laser, for example, may be used. The number of lasers is not limited, either. When a laser is used as a light source, an optical system for shaping a parallel light beam from a laser light source into a desired beam shape, and that for converting a coherent laser light beam into an incoherent light beam can be used. A light source which can be used in the light source unit is not limited to a laser, and one or a plurality of lamps such as mercury lamps or xenon lamps can also be used. The illumination optical system illuminates a mask, and includes, for example, a lens, mirror, light integrator, and stop.

The projection optical system 113 can be, for example, an optical system including only a plurality of lens elements, an optical system including a plurality of lens elements and at least one concave mirror, an optical system including a plurality of lens elements and at least one diffraction optical element such as a kinoform, or an optical system including only mirrors. The reticle stage 112 and substrate stage 114 can be moved by, for example, linear motors. The respective stages move in synchronism with each other. The substrate stage 114 and reticle stage 112 include actuators (driving mechanisms; not shown) in order to align the pattern of a reticle with a given position on a substrate.

An exemplary method of manufacturing a device such as a semiconductor integrated circuit device or a liquid crystal display device using the above-mentioned exposure apparatus will be described next. The device is manufactured by an exposure step of exposing a substrate using the above-mentioned exposure apparatus, a development step of developing the substrate exposed in the exposure step, and subsequent known steps of processing the substrate developed in the development step. The subsequent known steps include, for example, etching, resist removal, dicing, bonding, and packaging steps.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-201084, filed Aug. 31, 2009, which is hereby incorporated by reference herein in its entirety.

What is claimed is:

1. A foreign substance inspection apparatus which includes a light projecting unit that projects light onto a surface of an object to be detected, a detector that detects an intensity of scattered light as a component of the light, projected onto the surface by the light projecting unit, in association with a two-dimensional coordinate position on the surface, and a processing unit that determines a particle size of a foreign substance present on the surface based on the detection result obtained by the detector, wherein
a relationship between the intensity of the scattered light detected by the detector and the particle size of the foreign substance differs depending on the two-dimensional coordinate position on the surface, and
the processing unit
determines, a conversion curve to convert the intensity of the scattered light detected by the detector into the particle size of the foreign substance, in accordance with the two-dimensional coordinate position of the foreign substance detected by the detector, and
converts the intensity of the scattered light detected by the detector into the particle size of the foreign substance using the determined conversion curve.

2. The apparatus according to claim 1, wherein
the detector includes
a line sensor in which a plurality of photoelectric conversion elements are positioned in a first direction, and
a driving unit configured to drive said line sensor relative to the surface of the object to be detected in a second direction perpendicular to the first direction.

3. The apparatus according to claim 1, wherein
the conversion curve is given by one of an association table between the intensity of the scattered light detected by the detector and the particle size of the foreign substance, and a function of the intensity of the scattered light versus the particle size of the foreign substance.

4. The apparatus according to claim 1, wherein
the processing unit has the conversion curve including a plurality of conversion curves corresponding to a plurality of regions, respectively, on the surface, and, if the two-dimensional coordinate position of the foreign substance detected by the detector belongs to one of the plurality of regions, determines the conversion curve in the region, to which the two-dimensional coordinate position of the detected foreign substance belongs, as a conversion curve corresponding to the two-dimensional coordinate position of the foreign substance detected by the detector.

5. The apparatus according to claim 1, wherein
the processing unit has the conversion curve including a plurality of conversion curves corresponding to a plurality of regions, respectively, on the surface, and
letting n be the number of a plurality of regions, $(x_i, y_i)$ (for i=1 to n) be coordinate positions of points which fall within the plurality of regions and are representative of the plurality of regions, $S_i$ (for i=1 to n) be the plurality of conversion curves, $(x,y)$ be a coordinate position of an arbitrary point which falls outside the plurality of regions and is present on the surface, and S be a conversion curve at the arbitrary point,
the processing unit determines the conversion curve S at the arbitrary point which falls outside the plurality of regions and is present on the surface from the plurality of conversion curves $S_i$ using:

$$S = \frac{\sum_{i=1}^{n} \left[ S_i \times \{(x-x_i)^2 + (y-y_i)^2\}^{-0.5} \right]}{\sum_{i=1}^{n} \{(x-x_i)^2 + (y-y_i)^2\}^{-0.5}}.$$

6. An exposure apparatus which transfers a pattern of a reticle onto a substrate to expose the substrate, the apparatus comprising
an inspection apparatus configured to inspect a surface of the reticle for a foreign substance,
the inspection apparatus including
a light projecting unit configured to project light onto a surface of an object to be detected, a detector configured to detect an intensity of scattered light as a component of the light, projected onto the surface by said light projecting unit, in association with a two-dimensional coordinate position on the surface, and a processing unit configured to determine a particle size of a foreign substance present on the surface based on the detection result obtained by said detector,
wherein
a relationship between the intensity of the scattered light detected by the detector and the particle size of the foreign substance differs depending on the two-dimensional coordinate position on the surface, and
said processing unit
determines, a conversion curve to convert the intensity of the scattered light detected by the detector into the particle size of the foreign substance, in accordance with the two-dimensional coordinate position of the foreign substance detected by the detector, and converts the intensity of the scattered light detected by the detector into the particle size of the foreign substance using the determined conversion curve.

7. A method of manufacturing a device, the method comprising:

transferring a pattern of a reticle onto a substrate to expose the substrate using an exposure apparatus;

developing the exposed substrate; and processing the developed substrate to manufacture the device, wherein the exposure apparatus includes an inspection apparatus configured to inspect a surface of the reticle for a foreign substance, the inspection apparatus includes a light projecting unit configured to project light onto a surface of an object to be detected, a detector configured to detect an intensity of scattered light as a component of the light, projected onto the surface by the light projecting unit, in association with a two-dimensional coordinate position on the surface, and a processing unit configured to determine a particle size of a foreign substance present on the surface based on the detection result obtained by the detector, a relationship between the intensity of the scattered light detected by the detector and the particle size of the foreign substance differs depending on the two-dimensional coordinate position on the surface, and the processing unit determines, a conversion curve to convert the intensity of the scattered light detected by the detector into the particle size of the foreign substance, in accordance with the two-dimensional coordinate position of the foreign substance detected by the detector, and converts the intensity of the scattered light detected by the detector into the particle size of the foreign substance using the determined conversion curve.

* * * * *